(12) United States Patent
Twichell

(10) Patent No.: US 9,878,263 B2
(45) Date of Patent: Jan. 30, 2018

(54) SYSTEM AND METHOD FOR ACTUATING CONTROLLED STIMULATION OF A PATIENT IN A CONFINED MEDICAL POSITION

(71) Applicant: Mark Twichell, Fredonia, NY (US)

(72) Inventor: Mark Twichell, Fredonia, NY (US)

( * ) Notice: Subject to any disclaimer, the term of this patent is extended or adjusted under 35 U.S.C. 154(b) by 0 days.

(21) Appl. No.: 15/280,480

(22) Filed: Sep. 29, 2016

(65) Prior Publication Data

US 2017/0087482 A1 Mar. 30, 2017

Related U.S. Application Data

(60) Provisional application No. 62/234,848, filed on Sep. 30, 2015.

(51) Int. Cl.
| | |
|---|---|
| *A61G 15/00* | (2006.01) |
| *A61C 19/00* | (2006.01) |
| *A63H 33/40* | (2006.01) |
| *A63H 3/36* | (2006.01) |
| *A63H 29/16* | (2006.01) |
| *A61G 13/00* | (2006.01) |
| *A61B 17/00* | (2006.01) |

(52) U.S. Cl.
CPC ......... *A63H 33/40* (2013.01); *A61G 13/0018* (2013.01); *A61G 15/00* (2013.01); *A63H 3/36* (2013.01); *A63H 29/16* (2013.01); *A61B 2017/0073* (2013.01); *A61C 2203/00* (2013.01); *A61G 2200/14* (2013.01); *A61G 2203/70* (2013.01)

(58) Field of Classification Search
CPC ...... A61G 15/00; A61G 15/002; A61G 15/02; A61G 15/10; A61G 15/105; A61G 2200/14; A63H 29/16; A63H 33/40
USPC ................................ 297/217.1, 330; 433/33
See application file for complete search history.

(56) References Cited

U.S. PATENT DOCUMENTS

| | | | | |
|---|---|---|---|---|
| 2,738,168 A | * | 3/1956 | McBride | A61G 15/105 297/254 |
| 3,143,803 A | * | 8/1964 | Lunn | A61G 15/00 312/198 |
| 3,259,430 A | * | 7/1966 | Beach | A61C 19/00 297/182 |

(Continued)

*Primary Examiner* — Alexander Niconovich
(74) *Attorney, Agent, or Firm* — Vincent G. LoTempio; Kloss, Stenger & LoTempio; David T. Stephenson

(57) ABSTRACT

A system and method for actuating controlled stimulation of a patient in a confined medical position helps sooth and entertain a patient receiving medical treatment while resting on a support member, like a dental chair. The system provides a support member, and integrates at least one air actuated animated member, such as a mobile or figurine, proximal to the support member, to enable animated motion by the animated member through pressurized air. Pressurized air causes the animated members to articulate in animated, colorful movements. Audio signals are also generated by the animated member in response to the pressurized air. The animated member can be a mobile or a cartoon character with joints, axes, and limbs that move when engaged by pressurized air. The patient or caregiver control distribution of the pressurized air by manipulating a foot valve and an arm valve to control the animated members.

16 Claims, 6 Drawing Sheets

(56) References Cited

U.S. PATENT DOCUMENTS

| | | | | | |
|---|---|---|---|---|---|
| 3,484,941 | A | * | 12/1969 | Svard | A61C 17/04 |
| | | | | | 433/92 |
| 3,847,573 | A | * | 11/1974 | Gandrud | A61C 1/0007 |
| | | | | | 137/550 |
| 4,413,858 | A | * | 11/1983 | Beach | A61G 15/00 |
| | | | | | 297/217.1 |
| 4,606,328 | A | * | 8/1986 | Thoman | A61F 7/02 |
| | | | | | 446/199 |
| 5,467,002 | A | * | 11/1995 | Brooks | A61G 15/02 |
| | | | | | 297/330 |
| 5,730,497 | A | * | 3/1998 | Raymond | A61G 13/00 |
| | | | | | 297/408 |
| 6,406,294 | B1 | * | 6/2002 | Bell | A61G 15/00 |
| | | | | | 433/33 |
| 7,353,620 | B1 | * | 4/2008 | Houston | A45D 20/08 |
| | | | | | 34/90 |
| 7,506,927 | B1 | * | 3/2009 | Williams | A61K 9/007 |
| | | | | | 297/180.12 |
| 7,862,123 | B2 | * | 1/2011 | Baker | A47C 7/54 |
| | | | | | 297/115 |
| 8,938,888 | B1 | * | 1/2015 | Brown | A45D 20/00 |
| | | | | | 132/212 |
| 2003/0139693 | A1 | * | 7/2003 | Swift | A61G 15/00 |
| | | | | | 601/15 |
| 2011/0001012 | A1 | * | 1/2011 | Smith | A63H 27/08 |
| | | | | | 244/155 A |
| 2011/0025915 | A1 | * | 2/2011 | Daban | A47C 7/72 |
| | | | | | 348/552 |
| 2011/0059416 | A1 | * | 3/2011 | Lee | A61C 17/043 |
| | | | | | 433/33 |

\* cited by examiner

SYSTEM AND METHOD FOR ACTUATING CONTROLLED STIMULATION OF A PATIENT IN A CONFINED MEDICAL POSITION

CROSS REFERENCE OF RELATED APPLICATIONS

This application claims the benefits of U.S. provisional application No. 62/234,848, filed Sep. 30, 2015 and entitled AIR ACTIVATED SENSORY ADAPTED DENTAL ENVIRONMENTAL SYSTEM, which provisional application is incorporated by reference herein in its entirety.

FIELD OF THE INVENTION

The present invention relates generally to a system and method for actuating controlled stimulation of a patient in a confined medical position. More so, the system provides a support member that supports a patient on a support member, such as a dental chair, and positions at least one air actuated animated member proximally, and in view of the patient; whereby an air control portion generates pressurized air configured to create forced articulation of the limbs, mouth, and axes of the animated member; whereby the patient or the medical professional control distribution of the pressurized air with valves to manipulate the animated member; whereby articulation of the animated member in view of the patient helps to sooth and entertain the patient while receiving medical treatment.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Generally, a mobile is a type of kinetic sculpture constructed to take advantage of the principle of equilibrium. It consists of a number of rods, from which weighted objects or further rods hang. The objects hanging from the rods balance each other, so that the rods remain more or less horizontal. Each rod hangs from only one string, which gives it freedom to rotate about the string. Ensembles of these balanced parts hang freely in space, by design without coming into contact with each other.

Typically, a dental chair is used to support a patient receiving dental treatment. Dental chairs usually have adjustable height, with a foot-operated jack or a hand-operated lever on the side. Dental chairs are also configured to rotate or lean backwards. Dental chairs are normally made from metal, leather, and antibacterial vinyl materials, and are usually rather heavy.

It is known that upon seeing the variety of dental instruments, and being asked to open the mouth indefinitely, simply the thought of being confined in a dental chair causes unpleasant feelings in most patients. When the dental treatment commences, these feelings can become stronger, to the point of claustrophobic panic attacks caused by the constrained surrounding and disorientation from leaning back in the dental chair. These are known to cause feelings of concern, anxiety or even fear in the patient.

Other proposals have involved relieving anxiety of a patient. The problem with these systems is that they do not allow the patient to have any control in operation of the system. Even though the above cited patient anxiety relieving systems meet some of the needs of the market, a system and method for actuating relaxation of a patient in a confined medical position that provides a support member that supports a patient; and positions air actuated animated members proximally, and in view of the support member; and generates pressurized air to create forced articulation of the limbs, mouth, and axes of the animated member; and further allows the patient or the medical professional control distribution of the pressurized air with valves to manipulate the animated member is still desired.

SUMMARY

Illustrative embodiments of the disclosure are generally directed to a system and method for actuating controlled stimulation of a patient in a confined medical position. The system and method provides a support member that supports a patient, such as a chair or a table, and positions at least one air actuated animated member proximally, and in view of the support member. An air control portion generates pressurized air that is configured to create forced articulation of the limbs, mouth, and axes of the animated member, when engaged. The patient or the medical professional control distribution of the pressurized air by manipulating a foot valve, or an arm valve, or both to manipulate the animated member. In this manner, articulation of the animated member while in view of the patient helps to sooth and entertain the patient while receiving medical treatment from the medical professional.

In some embodiments, the system and method enables a medical professional and a patient to selectively direct air towards animated members; whereby the air pressure causes the animated members to articulate in animated, colorful movements. The animated member can be a mobile or a cartoon character with joints, axes, and limbs that allow for movement when air pressure is applied. Both the medical professional and the patient can cause the animated member to move. An air control portion generates and regulates air. A foot valve allows the medical professional to regulate air flow to the animated member. An arm valve allows a patient to direct air flow towards the animated member. The animated member may emit audio signals to further enhancing the entertainment aspects.

In one aspect of the present invention, a system for actuating controlled stimulation in a confined medical position, comprises:

a support member defined by a seat portion, an arm portion, and a base portion, the seat portion configured to support a substantial amount of the torso, the arm portion configured to at least partially support the arms, the base portion configured to enable support and manipulation of the support member;

an air control portion configured to generate pressurized air;

at least one animated member disposed proximally to the support member, the at least one animated member configured to articulate in response to the pressurized air, wherein the at least one animated member is at least partially viewable while supported on the support member, wherein articulation of the at least one animated member helps animate the at least one animated member;

a foot valve disposed proximal to the base portion of the support member, the foot valve configured to regulate the flow of the pressurized air to the at least one animated member;

an arm valve disposed integrally in the arm portion of the support member, the arm valve configured to regulate the flow of the pressurized air to the at least one animated member; and a plurality of tubes, the plurality of tubes configured to carry the pressurized air from the air control portion to the foot valve and the arm valve, the plurality of tubes further configured to carry the pressurized air from the foot valve and the arm valve to the at least one animated member, wherein manipulation of the foot valve and the arm valve selectively controls articulation of the at least one animated member.

In a second aspect, the support member is a dental chair.

In another aspect, manipulation of the support member includes at least one of the following movements: swiveling, reclining, raising, and lowering.

In another aspect, the air control portion comprises at least one of the following: an air compressor, a power switch, a discharge port to the foot valve, a discharge port to the arm valve, a discharge port to the animated member.

In another aspect, the at least one animated member includes at least one member selected from the group consisting of: an overhead mobile, a cartoon character, and a whirly-gig.

In another aspect, the foot valve has a foot toggle switch.

In another aspect, the foot valve is operable by a medical professional.

In another aspect, the arm valve has an arm toggle switch.

In another aspect, the arm valve is operable by a patient sitting in the support member.

In another aspect, the arm valve is accessible at the arm portion of the support member.

In another aspect, the plurality of tubes are vinyl plastic tubes.

One objective of the present invention is to provide an animated mobile, character, or whirly-gig that entertains a child receiving treatment in a dental chair.

Another objective is to enable a child to control the articulations of multiple characters or mobiles so as to sooth and entertain a child receiving dental treatment.

Another objective is to variably control the air pressure, so as to more precisely control the articulation of the animated member.

Another objective is to provide a finger controlled toggle switch on the arm rest of the dental chair for regulating air flow and pressure into, or proximal to the animated member.

Another objective is to provide a foot controlled toggle switch on the base portion of the dental chair, or behind the back rest of a dental chair for a medical professional to control the animated member.

Another objective is to provide multiple animated characters, mobiles, and characters placed on both the walls and ceiling of a dental treatment room that are visible from a dental chair in the upright position and the reclined position.

Another objective is to provide an inexpensive to manufacture system and method for actuating controlled stimulation of a patient in a confined medical position.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which.

Like reference numerals refer to like parts throughout the various views of the drawings.

DETAILED DESCRIPTION OF THE INVENTION

Figure 1:
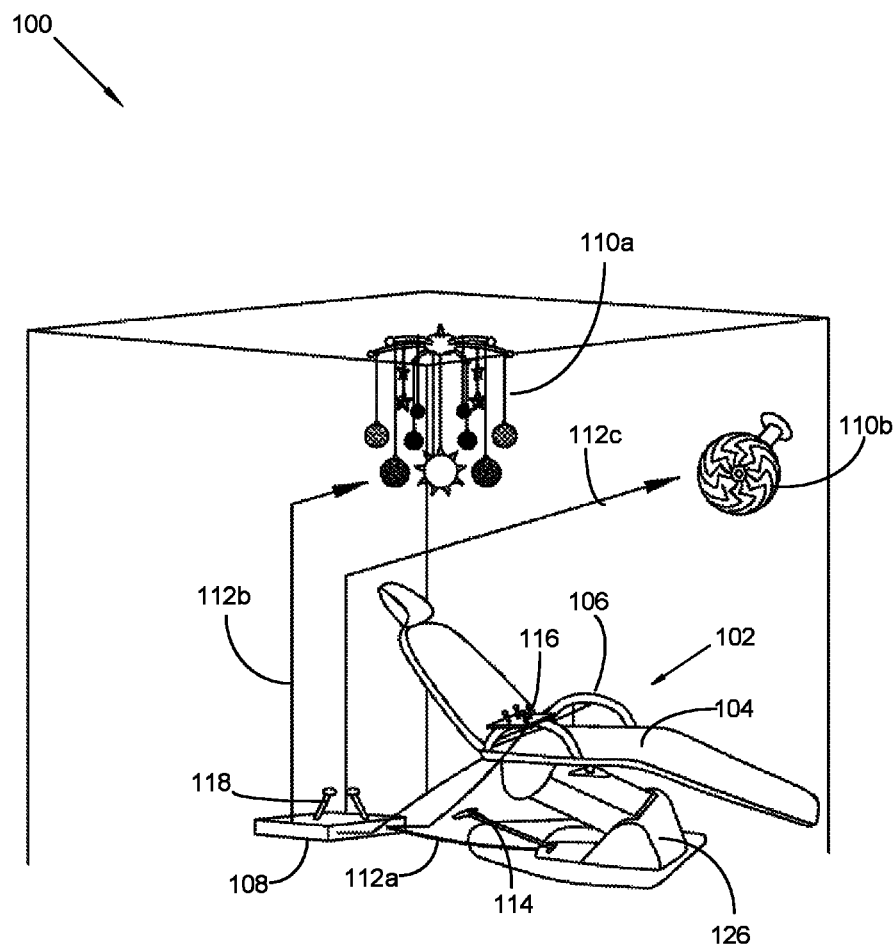
FIG. 1 illustrates a block diagram of an exemplary a system for actuating controlled stimulation in a confined medical position, in accordance with an embodiment of the present invention.

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

At the outset, it should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" of this invention as required by 35 U.S.C. §112.

In one embodiment of the present invention presented in FIGS. 1-6, a system 100 and method 200 for actuating controlled stimulation of a patient in a confined medical position, helps sooth and entertain a patient who is receiving treatment while resting on a support member 102, such as a dental chair. System 100 and method 200 enables both a medical professional and a patient to selectively direct pressurized air towards at least one animated member 110a, 110b, such as a mobile or figurine. The pressurized air causes animated member 110a to articulate in animated, colorful movements. The articulation of animated member 110a, 110b is designed to entertain and soothe the patient while receiving treatment and resting on support member 102.

Looking at FIG. 1, system 100 for actuating controlled stimulation of a patient in a confined medical position, hereafter "system 100" is unique in that both the medical professional and the patient may cause animated member 110a, 110b to actuate movement of animated member 110a, 110b. The patient has proximal access to an arm valve 116 to regulate pressurized air towards the animated member. The medical professional can also control the animated member while simultaneously providing medical treatment, through manipulation of a proximally disposed foot valve 114.

Another unique feature is that animated member 110a, 110b is visible from both the upright and reclined position from support member 102. Thus, the patient can view the animated member 110a, 110b while lying down on the back, the sides, or the stomach. Another unique feature is that animated member 110a, 110b may be configured to gesture, talk, and dance for the patient to provide directions related to the treatment, or to distract the patient's attention from the medical treatment.

In some embodiments, pressurized air is carried into ports and through channels inside the animated member to forcible move hinged components of the animated member 110a, 110b. Another unique feature is that the pressurized air is controlled through multiple valves and tubes. An arm valve, a foot valve provide control of the pressurized air, while various discharge ports 120, 122, 124 allow for controlled venting of excess air.

As referenced in FIG. 1, system 100 provides a unique support member 102 having integrated within, an air control portion 108 and at least one animated member 110a, 110b. The controlled manipulation of the animated member from the support member 102 helps soothe the patient during stressful moments while receiving medical treatment by providing at least one air-controlled, moving animated member 110a, 110b that is visible by the patient resting on support member 102. A plurality of tubes 112a, 112b, 112c, shown in FIG. 2, carry pressurized air to the animated members 110a, 110b to generate the animated articulation thereof.

For the present invention, the patient may include a child, an invalid, an elderly person, and a general medical patient. Support member 102 may include, without limitation, a dental chair, a hygiene chair, a medical bed, and a surgery table. The treatment being performed on the patient may include dental or medical related treatment performed by various medical professionals, including, without limitation, a dentist, a dental assistant, a doctor, a surgeon, a chiropractor, and a hygienist.

Those skilled in the art will recognize that patients, especially children, can have great apprehensions about dental treatment while sitting and receiving dental treatment in a dental chair. This is partially because the patient cannot see what is happening inside the mouth, and there may be pain associated with roots, nerves, and tooth removal procedures in the mouth. Furthermore, when a child is separated from a parent, the child may feel scared. Animated member 110a, 110b is disposed to be visible to the child in the support member, from both an upright position and an inclined position. Further, by enabling the child to control articulation of animated member 110a, 110b, the child feels more in control and thereby, focuses less on the actual dental treatment being performed.

System 100 comprises a support member 102 defined by a seat portion 104, a base portion 126, and an arm portion 106. The seat portion 104 provides a supportive back and buttocks supportive surface for the patient to sit and recline while receiving the dental treatment. Arm portion 106 provides a surface for the arms to rest, and also includes various valves for regulating the air pressure used to actuate the animated member 110a, 110b. Base portion 126 forms a foundation and enables the support member 102 to swivel, recline, raise, and lower for facilitating treatment of the patient. In one embodiment, support member 102 is a dental chair that is configured to operate in substantially the same way as dental chairs known in the art operate.

Figure 3:
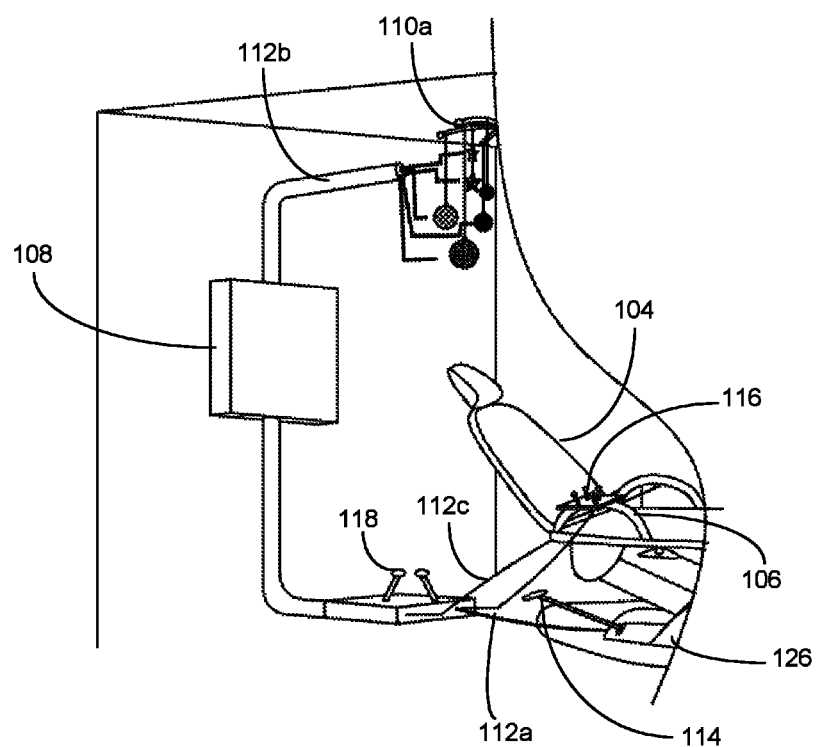
FIG. 3 illustrates a perspective view of an exemplary wall mounted animated member, in accordance with an embodiment of the present invention.

As FIG. 3 illustrates, system 100 provides at least one animated member 110a, 110b that is forcibly manipulated by air pressure to articulate joints, axes, and components. The articulation of animated member 110a, 110b is designed to entertain and soothe a patient who is receiving treatment in the support member 102. The patient may include a child, an invalid, and a general medical patient.

In one possible embodiment, animated member 110a, 110b is a model that depicts a cartoon character. The cartoon character is forcibly articulated in a variety of motions through pressurized air, so as to entertain and sooth a patient while receiving treatment. The animated member 110a, 110b is manipulated through the use of pressurized air that is generated at an air control portion 108 and carried directly into the animated member 110a, 110b, or proximal to animated member 110a, 110b; which in either case produces coordinated articulation of sections of animated member 110a, 110b. The articulation of animated member 110a, 110b is designed to produce an overall animated, colorful effect that helps distract the patient while receiving medical treatment.

Figure 4:
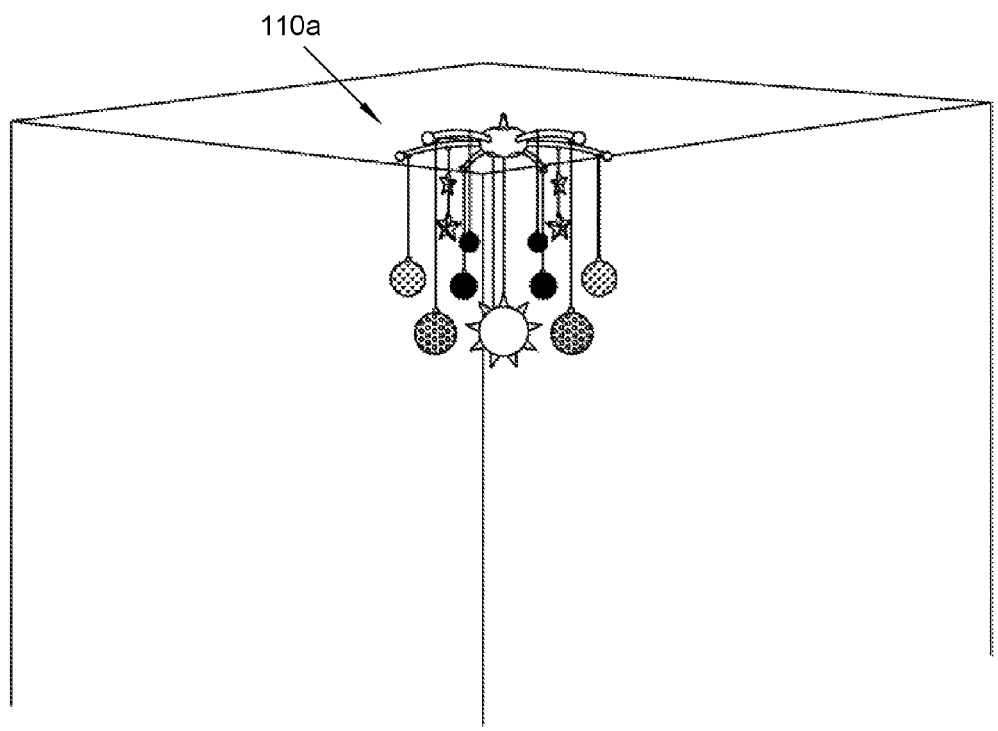
FIG. 4 illustrates a perspective view of an exemplary ceiling mounted animated member, in accordance with an embodiment of the present invention.

In one exemplary use, animated member 110a, 110b, may include, without limitation, an overhead mobile, a cartoon character, and a whirly-gig. Animated member 110a, 110b may be positioned on the wall or on the ceiling. For example, a wall mounted animated member 110a (FIG. 3) is visible from the upright position of a dental chair. A ceiling mounted animated member 110b is visible from a reclined position of the dental chair. FIG. 4 illustrates a perspective view of an exemplary ceiling mounted animated member.

In either position, animated member 110a, 110b is visible as viewed from the support member 102 in both the upright and reclined position. Animated member 110a, 110b may have various joints, axes, limbs, and loose mechanical components that move in coordination with the allocated air pressure when air is injected proximal to, or directly into animated member 110a, 110b.

Figure 2:
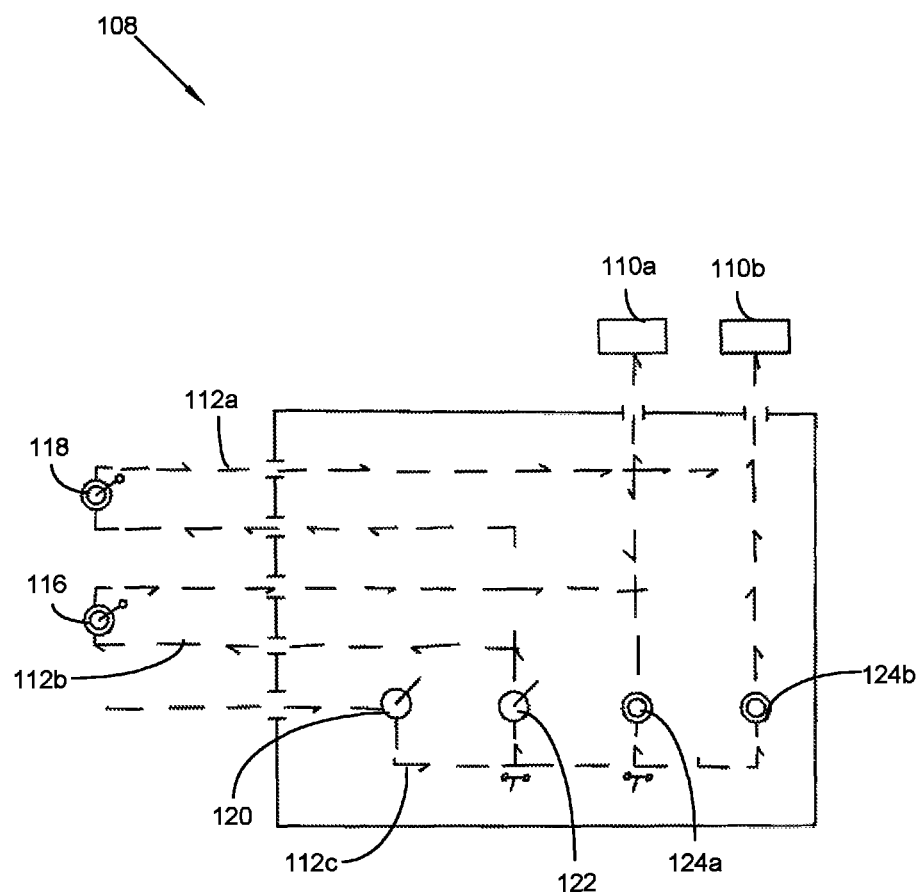
FIG. 2 illustrates a schematic diagram of an exemplary air control portion, showing the power switch, discharge ports, and accompanying tubes for carrying the air, in accordance with an embodiment of the present invention.

Looking back at FIG. 2, system 100 further comprises an air control portion 108 that is configured to generate pressurized air, and help regulate the flow of the generated air directly to, or proximally around animated member 110a, 110b. The pressurized air helps induce a desired movement of the animated member 110a, 110b. In this manner, the animated member 110a, 110b may be manipulated by the air to instruct the patient to perform activities, such as "lift the chin", "turn the head", "open wide" and the like. The use of the chair mounted controls encourages the patient to keep hands down thus avoiding interruption in treatment procedures from when hands are raised. In one alternative embodiment, animated member 110a, 110b includes an audio portion that emits voices, recordings, and music. This further animates the movements of animated member 110a, 110b and soothes the patient during treatment.

Air control portion 108 generates air at a predetermined air pressure. The air control portion 108 also controls dispersion of air pressure from the air control portion 108 to the animated member 110a, 110b. Air control portion 108 is configured to generate air pressure, regulate dispersion of the air pressure, and carry the air pressure to appropriate tubes and valves for actuation of the animated member 110a, 110b.

In one embodiment, air control portion 108 may include, without limitation, an air compressor for generating the air, a power switch 118 for powering on and off the air control portion 108, a discharge port 120 for directing the air to the foot valve 114, a discharge port 122 for directing the air to the arm valve 116, and a discharge port 124 for directing the air to the animated member 110a, 110b. In one exemplary embodiment, air control portion 108 utilizes multiple control switches mounted in parallel from arm valve 116 and foot valve 114.

One unique aspect of the present invention is that either the medical professional or the patient may control the flow of pressurized air from air control portion 108, and thereby selectively actuate movement by the animated member 110a, 110b. A foot valve 114 at the base portion of the support member 102 enables the provider to regulate air pressure with a foot while performing the treatment on the patient. Foot valve 114 enables the medical professional to divert compressed air to the arm valve 116 and the animated member 110a, 110b. Foot valve 114 is easy to manipulate while simultaneously providing treatment to the patient. Foot valve 114 may include a toggle switch. In one alternative embodiment, foot valve 114 is located behind the seat portion 104 of the support member 102, such as behind the back rest where a dentist can easily access to switch a toggle on and off.

As FIG. 1 shows, an arm valve 116 at the arm portion 106 of support member 102 enables the patient to regulate the air while comfortably resting in support member 102. In one embodiment, arm valve 116 may include a toggle switch that sits under an arm rest. Thus, the patient simply uses the fingers to manipulate the arm valve on top of the arm rest or beneath the arm rest.

Arm valve 116 enables the patient to direct a stream of pressurized air to the animated member 110a, 110b to create the desired articulation by the animated member 110a, 110b. Arm valve 116 is easy to manipulate while sitting in the support member 102. Foot valve 114 and the arm valve 116 are operatively connected through a plurality of tubes 112a, 112b, 112c that carry air from the air control portion 108 to the foot valve 114 and arm valve 116.

System 100 utilizes a plurality of tubes 112a, 112b, 112c to carry air between the valves 114, 116 described above. Tubes 112a, 112b, 112c may include vinyl plastic tubes known in the art to carry air in a medical environment. In one embodiment a tube 112a carries air from the air control portion 108 directly to the animated member 110a, 110b. In one embodiment, tube 112 enters a port on the animated member 110a, 110b. Upon entering port, the pressurized air is directed to the appropriate limb, axis, and joint through a pathway of channels inside animated member.

In another embodiment, tube 112b carries air from the air control portion 108 to foot valve 114. In another embodiment, a tube 112c carries air from air control portion 108 to the arm valve 116. Thus, from the foot valve 114 and arm valve 116, the air can be regulated to selectively engage animated member 110a, 110b.

Figure 5:
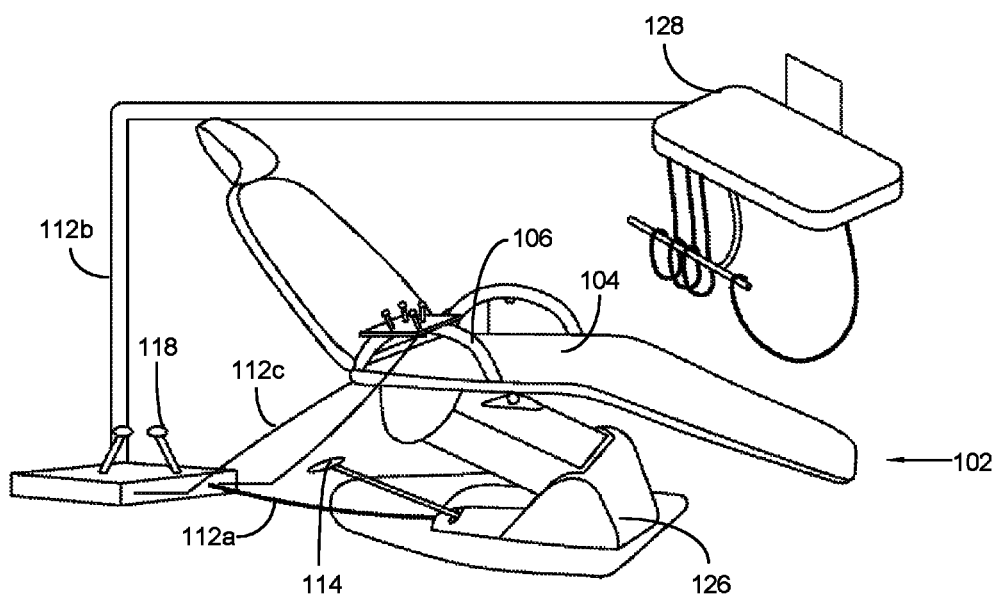
FIG. 5 illustrates a perspective view of the air control portion connected to a support member through a plurality of tubes that connect to a medical instrumentation portion, in accordance with an embodiment of the present invention.

FIG. 5 illustrates an alternative embodiment of system, wherein air control portion 108 provides a plurality of tubes 112a, 112b, 112c that connect to a medical instrumentation portion 128. Medical instrumentation portion may include medical instruments, such as drills, polishers, and other air actuated medical instrumentation known in the art. Here, pressurized air carried by tubes 112a-c actuates both animated member 110a, and other air actuated medical instruments.

Figure 6:
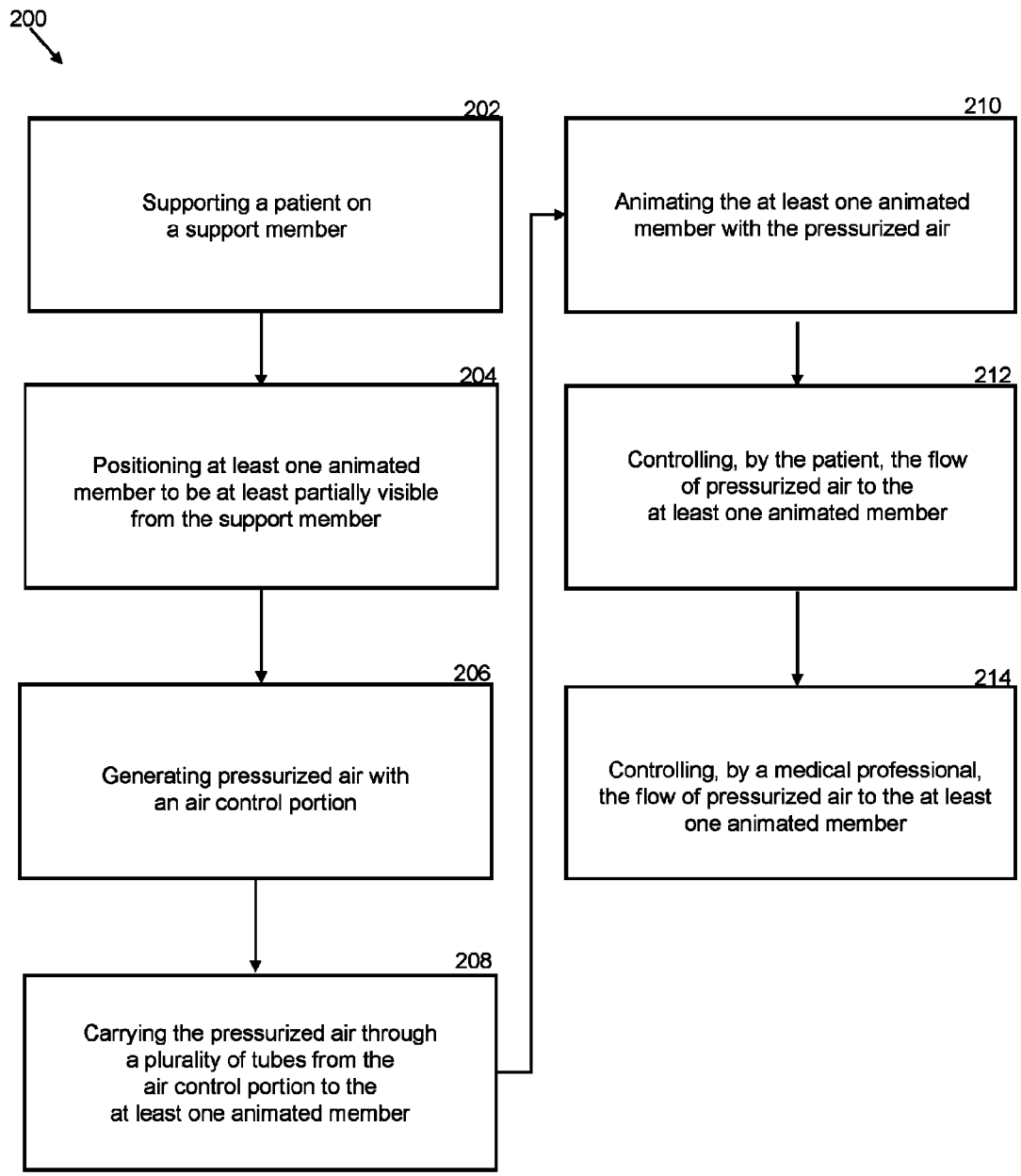
FIG. 6 illustrates a method for actuating controlled stimulation of a patient in a confined medical position, in accordance with an embodiment of the present invention.

FIG. 6 illustrates an exemplary method 200 for actuating controlled stimulation in a confined medical position. Method 200 may include an initial Step 202 of supporting a patient in a support member. Support member 102 defined by a seat portion 104, a base portion 126, and an arm portion 106. Seat portion 104 provides a supportive back and buttocks supportive surface for the patient to sit and recline while receiving the dental treatment.

Arm portion 106 provides a surface for the arms to rest, and also includes various valves for regulating the air pressure used to actuate the animated member 110a, 110b. Base portion 126 forms a foundation and enables the support member 102 to swivel, recline, raise, and lower for facilitating treatment of the patient.

Another Step 204 comprises positioning at least one animated member to be at least partially visible from the support member. Animated member 110a, 110b, may include, without limitation, an overhead mobile, a cartoon character, and a whirly-gig. Animated member 110a, 110b may be positioned on the wall or on the ceiling.

A Step 206 may include generating pressurized air with an air control portion. Air control portion 108 that is configured to generate pressurized air, and help regulate the flow of the generated air directly to, or proximally around animated member 110a, 110b. The pressurized air helps induce a desired movement of the animated member 110a, 110b.

A Step 208 comprises carrying the pressurized air through a plurality of tubes from the air control portion to the at least one animated member. Tubes 112a, 112b, 112c to carry air between the valves 114, 116 described above. Tubes 112a, 112b, 112c may include vinyl plastic tubes known in the art to carry air in a medical environment. In one embodiment a tube 112a carries air from the air control portion 108 directly to the animated member 110a, 110b.

A Step 210 comprises animating the at least one animated member with the pressurized air. The pressurized air helps induce a desired movement of the animated member 110a, 110b. In this manner, the animated member 110a, 110b may be manipulated by the air to instruct the patient to perform activities, such as "lift the chin", "turn the head", "open wide", and the like.

In some embodiments, a Step 212 may include controlling, by the patient, the flow of pressurized air to the at least one animated member. The medical professional may control the flow of pressurized air from air control portion 108, and thereby selectively actuate movement by the animated member 110a, 110b.

A Step 214 comprises controlling, by a medical professional, the flow of pressurized air to the at least one animated member. The medical professional may control the flow of pressurized air from air control portion 108, and thereby selectively actuate movement by the animated member 110a, 110b. A foot valve 114 at the base portion of the support member 102 enables the provider to regulate air pressure with a foot while performing the treatment on the patient. Foot valve 114 enables the medical professional to divert compressed air to the arm valve 116 and the animated member 110a, 110b.

In an alternative embodiment of method 200, a step comprises performing a medical procedure on the patient while simultaneously animating the at least one animated member. Arm valve 116 may include a toggle switch that sits under an arm rest. Thus, the patient simply uses the fingers to manipulate the arm valve on top of the arm rest or beneath the arm rest. Arm valve 116 enables the patient to direct a stream of pressurized air to the animated member 110a, 110b to create the desired articulation by the animated member 110a, 110b.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What I claim is:

1. A system for actuating controlled stimulation of a patient having a torso and arms in a confined medical position, the system comprising:
   a support member defined by a seat portion, an arm portion, and a base portion, the seat portion configured to support a substantial amount of the torso, the arm portion configured to at least partially support the arms, the base portion configured to enable support and manipulation of the support member;
   an air control portion configured to generate pressurized air;
   at least one animated member disposed proximally to the support member, the at least one animated member configured to articulate in response to the pressurized air,
   wherein the at least one animated member is at least partially viewable while supported on the support member,
   wherein articulation of the at least one animated member helps animate the at least one animated member;
   a foot valve disposed proximal to the base portion of the support member, the foot valve configured to regulate a flow of pressurized air to the at least one animated member;
   an arm valve disposed integrally in the arm portion of the support member, the arm valve configured to regulate the flow of the pressurized air to the at least one animated member; and
   a plurality of tubes, the plurality of tubes configured to carry the pressurized air from the air control portion to the foot valve and the arm valve, the plurality of tubes further configured to carry the pressurized air from the foot valve and the arm valve to the at least one animated member,
   wherein manipulation of the foot valve and the arm valve selectively controls articulation of the at least one animated member.

2. The system of claim 1, wherein the support member is a dental chair.

3. The system of claim 1, wherein manipulation of the support member includes at least one of the following movements: swiveling, reclining, raising, and lowering.

4. The system of claim 1, wherein the air control portion comprises at least one of the following: an air compressor, a power switch, a discharge port of the foot valve, a discharge port of the arm valve, a discharge port of the at least one animated member.

5. The system of claim 1, wherein the at least one animated member includes at least one member selected from the group consisting of: an overhead mobile, a cartoon character, and a whirly-gig.

6. The system of claim 1, wherein the foot valve comprises a foot toggle switch.

7. The system of claim 1, wherein the foot valve is operable by a medical professional.

8. The system of claim 1, wherein the arm valve comprises an arm toggle switch.

9. The system of claim 1, wherein the arm valve is operable by a patient.

10. The system of claim 1, wherein the arm valve is accessible at the arm portion of the support member.

11. The system of claim 1, wherein the plurality of tubes carry air to a medical instrumentation portion.

12. A system for actuating controlled stimulation of a patient having a torso and arms in a confined medical position, the system comprising:
    a support member defined by a seat portion, an arm portion, and a base portion, the seat portion configured to support a substantial amount of the torso, the arm portion configured to at least partially support the arms, the base portion configured to enable support and manipulation of the support member;
    an air control portion configured to generate pressurized air, the air control portion comprising at least one of the following: an air compressor, a power switch, and at least one discharge port;
    at least one animated member disposed proximally to the support member, the at least one animated member configured to articulate in response to the pressurized air,
    wherein the at least one animated member is at least partially viewable while supported on the support member,
    wherein articulation of the at least one animated member helps animate the at least one animated member;
    a foot valve disposed proximal to the base portion of the support member, the foot valve configured to regulate a flow of pressurized air to the at least one animated member;
    an arm valve disposed integrally in the arm portion of the support member, the arm valve configured to regulate the flow of the pressurized air to the at least one animated member; and
    a plurality of tubes, the plurality of tubes configured to carry the pressurized air from the air control portion to the foot valve and the arm valve, the plurality of tubes further configured to carry the pressurized air from the foot valve and the arm valve to the at least one animated member,
    wherein manipulation of the foot valve and the arm valve selectively controls articulation of the at least one animated member.

13. The system of claim 12, wherein the support member is a dental chair.

14. The system of claim 12, wherein manipulation of the support member includes at least one of the following movements: swiveling, reclining, raising, and lowering.

15. The system of claim 12, wherein the at least one discharge port comprises at least one of the following: a discharge port of the foot valve, a discharge port of the arm valve, and a discharge port of the at least one animated member.

16. The system of claim 12, wherein the at least one animated member includes at least one member selected from the group consisting of: an overhead mobile, a cartoon character, and a whirly-gig.

\* \* \* \* \*